United States Patent
Gray

(10) Patent No.: US 9,066,909 B2
(45) Date of Patent: *Jun. 30, 2015

(54) METHODS FOR PRODUCING AND USING REJUVENATED RED BLOOD CELLS

(71) Applicant: Biomet Biologics, LLC, Warsaw, IN (US)

(72) Inventor: Alan Gray, North Reading, MA (US)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/756,021

(22) Filed: Jan. 31, 2013

(65) Prior Publication Data

US 2014/0065117 A1 Mar. 6, 2014

Related U.S. Application Data

(60) Provisional application No. 61/697,644, filed on Sep. 6, 2012.

(51) Int. Cl.
*A01N 63/00* (2006.01)
*A61K 35/18* (2015.01)
*A61K 31/19* (2006.01)
*A61K 31/70* (2006.01)
*A01N 1/02* (2006.01)

(52) U.S. Cl.
CPC ............... *A61K 35/18* (2013.01); *A61K 31/19* (2013.01); *A61K 31/70* (2013.01); *A01N 1/0226* (2013.01)

(58) Field of Classification Search
USPC ............ 424/93.71; 210/782; 435/2; 604/6.03
See application file for complete search history.

(56) References Cited

U.S. PATENT DOCUMENTS

| | | | |
|---|---|---|---|
| 5,250,303 A | 10/1993 | Meryman et al. | |
| 7,723,017 B2 | 5/2010 | Bitensky et al. | |
| 2005/0074743 A1* | 4/2005 | Purmal et al. | 435/1.1 |
| 2005/0233302 A1 | 10/2005 | Hess et al. | |
| 2011/0256522 A1 | 10/2011 | Ericson et al. | |
| 2012/0077182 A1* | 3/2012 | Bitensky et al. | 435/2 |
| 2013/0004937 A1* | 1/2013 | Yoshida et al. | 435/2 |

FOREIGN PATENT DOCUMENTS

| | | |
|---|---|---|
| WO | 0113933 A2 | 3/2001 |
| WO | 2011103179 A1 | 8/2011 |
| WO | 2014039660 A1 | 3/2014 |

OTHER PUBLICATIONS

Brecher, M.E. et al. Rejuvenation of erythrocytes preserved with AS-1 and AS-3. A.J. Clin. Path. 96(6):767-769. 1991.
Burger, Patrick et al. An improved red blood cell additive solution maintains 2, 3-diphosphoglycerate and adenosine triphosphate levels by an enhancing effect on phosphofructokinase activity during cold storage. Transfusion, vol. 50, No. 11, (Nov. 29, 2010), pp. 2386-2392.
Button, L. et al. "Rejuvenation of red blood cells drawn in ADSOL to extend autologous red cell storage" (Abstract S54) Transfusion 26(6): 558, 1986.
D'Alessandro, Angelo et al. Red blood cell strage: the story so far. Blood Transfus, (Mar. 29, 2010), pp. 82-88.
Haemonetics, ACP 215 Automated Cell Processor (2012).
Heaton, A. et al. "Use of ADSOL preservation solution for prolonged storage of low viscosity AS-1 red blood cells." BR. J. Haemo. 57:467-468, 1984.
Hess, J.R. An update on solutions for red cell storage. Vox Sanguinis, vol. 91, No. 1 (Jul. 1, 2006) pp. 13-19.
Hess, John R., Red cell storage. Journal of Proteomics, Elsevier, Amsterdam, NL, vol. 73, No. 3, (Jan. 3, 2010), pp. 368-373.
Klein et al., "Red Blood Cell Transfusion in Clinical Practice" The Lancet, (Aug. 4, 2007), vol. 370, pp. 415-426.
Liu et al., "Microfluidic Chip Toward Cellular ATP and ATP-Conjugated Metabolic Analysis with Bioluminescence Detection" Analytical Chemistry, (Jan. 15, 2005), vol. 77, No. 2, pp. 573-578.
Lockwood et al. "Effects of Rejuvenation and Frozen Storage on 42-Day-Old AS-3 RBCs" Transfusion, (Nov. 2003) vol. 43, pp. 1527-1532.
Rathburn, E.J. "Posttransfusion survival of red cells frozen for 8 weeks after 42-day liquid storage in AS-3." Transfusion 29(3):213-217, 1989.
Rejuvenation Handbook, A Comprehensive Guide to Red Cell Rejuvenation, enCyte™ Systems Inc., Brochure, (1977).
reJuvesol® Red Blood Cell Processing Solution, enCyte™ Systems, Inc., Brochure (Mar. 1997).
Reynolds JD, et al. "The Transfusion Problem: Role of Aberrant S-Nitrosylation" Transfusion, 51:852-858, 2011.
Roback JD, "Vascular Effects of the Red Blood Cells Storage Lesion" Transfusion Medicine, ASH Education Book. Dec. 10, 2011 vol. 2011 No. 1 475-479.
Song et al. "Multiplexed volumetric bar-chart chip for point-of-care diagnostics" Nat Commun. (2012) 3:1283.
Spiess et al. Pro: Autologous blood should be available for elective cardiac surgery. Journal of Cardio Thoracic and Vascular Anesthesia, Saunders, Philadelphia, PA, US, vol. 8, No. 2 (Apr. 1, 1994), pp. 231-237.

(Continued)

*Primary Examiner* — Ralph Gitomer
(74) *Attorney, Agent, or Firm* — Harness, Dickey

(57) ABSTRACT

Methods for treating blood. The methods comprise obtaining whole blood from a donor, mixing the whole blood with a red blood cell enhancement composition, and incubating the mixture of whole blood and red blood cell enhancement composition. The method can be performed at a time proximate to the time of obtaining blood from the donor, or after the blood has been stored for a period of time. The method rejuvenates red blood cells.

11 Claims, No Drawings

(56) References Cited

OTHER PUBLICATIONS

Valeri, C.R. et al., "Automation of the glycerolization of red blood cells with the high-separation bowl in the Haemonetics ACP 215 Instrument" Transfusion 2005, vol. 45, p. 1621-1627.

Valeri, C.R. et al. The survival, function and hemolysis of human RBCs stored at 4C in additive solution (AS-1, AS-3 or AS-5) for 42 days and then biochemically modified, frozen, thawed washed and stored at 4C in sodium chloride and glucose solution for 24 hours. Transfusion, American Association of Blood Banks, Bethesda, MD, US, vol. 40 (Nov. 1, 2000), pp. 1341-1345.

Valeri, C.R., Rejuvenation and Freezing of Outdated Stored Human Red Cells, New England Journal of Medicine 287:1.307-1313 (Dec. 28, 1972).

Valeri, C.R. "Simplification of the method for adding and removing glycerol during freezing preservation of human red blood cells with the high or low glycerol methods: Biochemical Modification prior to freezing." Trasfusion 15 (3):195-218, 1975.

Valeri, C.R. et al. "A clinical experience with ADSOL preserved erythrocytes" Surg. Gyn. Obs. 166:33-46, 1988.

Van De Watering, L.M. G, et al. Beneficial Effects of Leukocyte Depletion of Transfused Blood on Postoperative Complications in Patients Undergoing Cardiac Surgery: A Randomized Clinical Trial. Circulation, vol. 97, No. 6, (Feb. 17, 1998), pp. 562-568.

Veale, Margaret F. et al. Effect of additive solutions on red blood cell (RBC) membrane properties of stored RBCs prepared from whole blood held for 24 hours at room temperature. Transfusion Jan. 2011, vol. 51, Suppl 1, (Jan. 2011), pp. 255-335.

Yoshida, T., et al. The effects of additive solution pH and metabolic rejuvenation on anaerobic storage of red cells, Transfusion, vol. 48, No. 10, (Oct. 1, 2008), pp. 2096-2105.

Zimrin, A.B. et al. Current issues relating to the transfusion of stored red blood cells. Vox Sanguines, vol. 96, No. 2, (Feb. 1, 2009), pp. 93-103.

COBE 2991 "Cell Processor." TherumoBCT. 2008, 4 pages.

Meyer, E. K. et al. "Rejuvenation capacity of red blood cells in additive solutions over long-term storage." Transfusion. Jul. 2011, vol. 51, No. 7: 1574-1579.

Resnick, et al. A. J. Medical Sciences, 1994, Feb 307, Suppl. 1, SS66-9, Abstract Only.

Scott, K. L. et al. "Biopreservation of Red Blood Cells: Past, Present, and Future" Transfusion Medicine Reviews, Grune and Stratton, Orlando, FL (2005) vol. 19 No. 2: 127-142.

* cited by examiner

METHODS FOR PRODUCING AND USING REJUVENATED RED BLOOD CELLS

This application claims benefit to provisional application 61/697,644 filed Sep. 6, 2012.

INTRODUCTION

The present technology relates to methods for producing "rejuvenated" red blood cells having improved metabolic activity. The technology also provides methods of administering such treated blood cells to mammalian subjects.

Transfusion of blood is an important aspect of treating many disorders and injuries, such as treatment of accident victims and during surgical procedures. According to current American Red Cross statistics, about 5 million people receive blood transfusions yearly in the United States alone. A single accident victim can require as many as 100 pints of blood. Thus, the collection and distribution of blood and blood products is a vital part of the health care system. Typically, blood is obtained from a donor and then processed and stored; units of stored blood or blood products are then taken from storage as needed and transfused into a patient in need. In some cases, the blood may be an autologous donation, where an individual donates blood in expectation of receiving his or her own blood by transfusion during a medical procedure.

Donated blood is typically processed into components and then placed in storage until needed. Short term storage can be as long as six weeks, although blood or blood components can be frozen and stored for as long as ten years. Unfortunately, the storage of red blood cells (RBCs) is associated with "storage lesions," altering their energy production, oxygen delivery capacity, redox status, and structural/membrane integrity. For example, the concentration of adenine triphosphate (ATP) in stored RBCs decreases over time. Not only is ATP an energy source used by cells to catalyze numerous enzymatic reactions, ATP also signals endothelial cells to release nitric oxide (NO), which is a potent vasodilator. Additionally, the concentration of 2,3-diphosphoglycerate (2,3-DPG) within RBCs is significantly reduced after 14 days of storage, and is often undetectable after 21 days of storage. 2,3-DPG enhances the ability of RBCs to release oxygen by interacting with deoxygenated hemoglobin, decreasing the hemoglobin's affinity for oxygen, and thereby promoting the release of the remaining oxygen bound to the hemoglobin. Therefore, with diminished levels of ATP and 2,3-DPG, an RBC's ability to oxygenate tissue is severely impaired.

To rejuvenate RBCs before administration into a patient, blood can be incubated with an RBC processing solution containing materials that increase intracellular concentrations of 2,3-DPG and ATP, improving the ability of RBCs to oxygenate tissues. Such RBC processing solutions typically comprise one or more active materials such as inosine, adenine, sodium pyruvate and sodium phosphate (dibasic and monobasic). A useful RBC processing solution is rejuvesol® Red Blood Cell Processing Solution (rejuvesol® Solution), which has been marketed by Cytosol Laboratories Inc. (now Citra Labs, LLC) since 1991.

While such compositions are effective to improve the metabolic activity of RBCs, there remains a need to develop compositions and methods that improve efficacy. Moreover, it has been discovered that such compositions may have particular utility during medical procedures treating certain disorders.

SUMMARY

The present technology provides methods of treating whole blood or whole blood fractions containing red blood cells using a red blood cell ("RBC") enhancement composition, such as for treatment of "storage lesions" that adversely affect the energy production, oxygen delivery capacity, redox status, and structural/membrane integrity of RBCs. Compositions comprise an RBC rejuvenating material selected from the group consisting of inosine, adenine, pyruvate, phosphate, and mixtures thereof. In various embodiments, processing improves nitric oxide bioavailability in the red blood cells. In some methods, the processing comprises processing of a blood fraction which has a reduced level of leukocytes compared to whole blood.

The present technology also provides methods for treating blood, comprising: obtaining whole blood or fraction containing RBCs from a donor, mixing the blood with an RBC enhancement composition, and incubating the mixture of blood and RBC enhancement composition. The method can be performed proximate to the time that the blood is obtained from the donor, or it can be performed after the blood has been stored for a period of time. Additionally, all or a fraction of the leukocytes can be removed from the blood to form leukoreduced blood. Leukoreduced blood can be produced prior to the processing. The RBC enhancement composition can comprise inosine, pyruvate, adenine, and phosphate.

The present technology further provides methods for increasing the metabolic activity of RBCs. Such a method comprises: obtaining whole blood from a donor, removing the leukocytes from the whole blood to produce a volume of leukoreduced blood, mixing the leukoreduced blood with an RBC processing solution, and incubating the mixture of leukoreduced blood and RBC processing solution. Increasing the metabolic activity of RBCs includes increases the levels of ATP, 2,3-DPG, and red blood cell-derived NO. The method can be performed immediately after blood is obtained from the donor, or it can be performed after the blood has been stored for a period of time. When the blood has been stored for a period of time, the leukocytes can be removed from the blood either before or after the blood has been placed in storage. The RBC enhancement composition can comprise inosine, pyruvate, adenine, and phosphate.

The present technology also provides methods for treating a disorder characterized by reduced tissue oxygenation in a mammalian subject comprising: mixing blood with an RBC enhancement composition, incubating the mixture of blood and RBC enhancement composition, and administering the incubated blood to the subject in need thereof. The blood can be autologous or the blood can be from a donor who is not the subject in need of the treatment. The technology contemplates scenarios wherein the blood has been kept in storage, and also wherein the blood has been obtained proximate to the time of treatment. Also, leukocytes can be removed from the blood prior to mixing the blood with the RBC processing solution.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology relates to methods of processing whole blood or a blood fraction comprising red blood cells (herein, unless specifically stated otherwise, referred to as "blood") using an RBC metabolic enhancement composition (referred to herein as an "enhancement composition"). Such compositions may comprise a rejuvenating material selected from the group consisting of inosine, adenine, pyruvate, phosphates, and mixtures thereof.

RBC Metabolic Enhancement Compositions

The present technology provides enhancement compositions which restore, increase or otherwise enhance, directly or indirectly, one or more metabolic functions of red blood cells. As further discussed below, in some embodiments, enhancement compositions increase the production or concentration of one or more intracellular constituents associated with the biochemical or biomechanical function of red blood cells, including oxygen transport, oxygen release or other metabolic parameters which affect the ability of blood to oxygenate tissue. As discussed further below, in some embodiments enhancement compositions increase the intracellular concentrations of adenine triphosphate (ATP) and 2,3-diphosphoglycerate (2,3-DPG).

In some embodiments, enhancement compositions the present technology can comprise safe and effective amounts of a rejuvenating material, such as inosine, pyruvate, adenine and phosphate. A "safe and effective" amount of a rejuvenating material is an amount that is sufficient to have the desired effect on biochemical or biomechanical function of RBCs, without undue adverse side effects on the viability of RBCs or other blood components or a subject to whom the RBCs are administered (such as toxicity, irritation, or allergic response), commensurate with a reasonable benefit/risk ratio when used in the manner of this technology. The specific safe and effective amount of the rejuvenating material will, obviously, vary with such factors as the metabolic state of the RBCs, the specific rejuvenating material(s) used, the conditions under which the RBCs are processed with the rejuvenating material, and physical condition of the subject to whom the RBCs are administered.

In various embodiments, the inosine can have a concentration of from about 25 g/L to about 30 g/L. Preferably, the concentration of inosine can be about 25.0 g/L, about 25.5 g/L, about 26.0 g/L, about 26.2 g/L, about 26.4 g/L, about 26.6 g/L, about 26.8 g/L, about 27.0 g/L, about 27.5 g/L, about 28.0 g/L, about 28.5 g/L, about 29.0 g/L, about 29.5 g/L, or about 30.0 g/L. In various embodiments, the pyruvate can have a concentration of from about 5 g/L to about 15 g/L. Preferably, the concentration of pyruvate can be about 5 g/L, about 6 g/L, about 7 g/L, about 8 g/L, about 9 g/L, about 10 g/L, about 11 g/L, about 12 g/L, about 13 g/L, about 14 g/L, or about 15 g/L. In various embodiments, the adenine can have a concentration of from about 0.2 g/L to about 2 g/L. Preferably, the concentration of adenine can be about 0.2 g/L, about 0.3 g/L, about 0.4 g/L, about 0.5 g/L, about 0.6 g/L, about 0.7 g/L, about 0.8 g/L, about 0.9 g/L, about 1.0 g/L, about 1.1 g/L, about 1.2 g/L, about 1.3 g/L, about 1.4 g/L, about 1.5 g/L, about 1.6 g/L, about 1.7 g/L, about 1.8 g/L, about 1.9 g/L, or about 2.0 g/L. The phosphate can be a mixture of a monobasic monohydrate salt and a dibasic heptahydrate salt. The phosphate can be a salt of sodium phosphate. The ratio of monobasic salt to dibasic salt can be from about 1:2 to about 1:3. More specifically, the monobasic salt:dibasic salt ratio can be about 1:2.0, about 1:2.10, about 1:2.15, about 1:2.20, about 1:2.25, about 1:2.30, about 1:2.35, about 1:2.40, about 1:2.45, about 1:2.50, about 1:2.55, about 1:2.60, about 1:2.65, about 1:2.70, about 1:2.75, about 1:2.80, about 1:2.85, about 1:2.90, about 1:2.95, or about 1:3.0. The phosphate mixture can have a final concentration of from about 18 g/L to about 22 g/L. More specifically, the concentration of phosphate mixture can be about 18 g/L, about 18.5 g/L, about 19 g/L, about 19.5 g/L, about 20 g/L, about 20.1 g/L, about 20.2 g/L, about 20.3 g/L, about 20.4 g/L, about 20.5 g/L, about 20.6 g/L, about 20.7 g/L, about 20.8 g/L, about 20.9 g/L, about 21 g/L, about 21.5 g/L, or about 22 g/L.

In some embodiments, RBC enhancement composition comprise:
(a) about 27 (e.g., 26.8) g/L inosine;
(b) about 11 g/L pyruvate (e.g., sodium pyruvate);
(c) about 0.7 (e.g., 0.681) g/L adenine; and
(d) about 21 (e.g., 20.8) 1 g/L phosphate (e.g., a mixture of about 6.21 g/L monobasic, monohydrate; and about 14.6 g/L dibasic, heptahydrate).

Preferably, the composition has a pH of from about 6.5 to about 7.5, more preferably from about 6.6 to about 7.4, more preferably from about 6.7 to about 7.1, more preferably from about 6.7 to about 7.0. An RBC enhancement composition useful in the methods of this technology is rejuvesol® Red Blood Cell Processing Solution (rejuvesol® Solution), which has been marketed by Citra Labs, LLC.

Methods of Processing

Methods of the present technology comprise, for example:
(1) mixing blood with an RBC enhancement composition; and
(2) incubating the mixture of blood and RBC enhancement composition.

The blood processed in the present methods may be obtained from a mammalian subject (a "donor") using methods among those well known in the art. In various embodiments the donor is a human subject. The blood may be allogeneic (i.e., donated by a subject of the same species) or autologous (obtained by the subject to whom the treated blood is to be administered, such as may be drawn in advance of a surgical procedure).

Processing of the blood using an RBC enhancement composition of the present technology may be performed on blood that has been stored or may be performed on "fresh" blood at a time proximate to the time it is withdrawn from the donor. As used herein, a "proximate" time is any time 24 hours or less after an initial event (e.g., donation of blood), such as concurrent with the event, or 18 hours, 12 hours, 6 hours, 4 hours, 2 hours, 1 hour, 30 minutes, 15 minutes, 10 minutes, 2 minutes, 1 minute, or less, after the initial event. Storage may be, for example, from 1 to 50 days, or longer, as needed. Storage may be at any temperature and other conditions to as to maintain viability of the RBCs for clinically acceptable storage period. For example, storage may be at a temperature of from about 1° C. to about 6° C. In other embodiments, the RBCs may be frozen, at a temperature of about −65° C. or lower, with the addition of conditioning agents that preserve the viability of the RBCs at such low temperatures. Suitable conditioning agents (cryopreservatives) include glycerol. It is understood that such conditioning agents are to be removed from the RBCs prior to administration, such as by methods described below for the removal of cryopreservatives prior to administration.

Incubating the mixture is conducted for a time sufficient to allow RBCs in the blood to assimilate components from the enhancement composition and achieve a desired effect on a biochemical or biomechanical function of RBCs. For example, incubation is conducted for a time sufficient to increase the concentration of ATP and 2,3-DPG in RBCs. The time may vary, depending on such factors as the desired level of increase of ATP and 2,3-DPG, the use of mechanical agitation, the amount of RBC enhancement composition used, and temperature of the blood during incubation. In some embodiments, about 50 ml of RBC enhancement composition is added to RBCs derived from up to about 550 ml of whole blood. Mixing can be performed by swirling, shaking, rotating, or agitating.

In some embodiments, the blood is tested during incubation to determine whether one or more desired biochemical or biomechanical attributes of the RBCs have been attained. Thus, for example, incubation may be conducted until a desired level of ATP, 2,3-DPG, NO or other biochemical marker of RBC function is attained, e.g., essentially equal to levels found in fresh blood.

Methods for measuring such markers of RBC function useful herein include methods among those known in the art. For example, 2,3-DPG can be detected by assay kits that are commercially available. In one such assay, 2,3-DPG from blood is split by phosphoglycerate mutase (PGM), when PGM is activated by glycolate-2-phosphate, to produce phosphoglycerate (PG) and inorganic phosphate (Pi). Both 2-PG and 3-PG can be formed, but 2-PG is isomerized by PGM to form 3-PG. In the presence of ATP, 3-PG is converted to 1,3-DPG by phosphoglycerate kinase (PGK). Next, 1,3-DPG is converted to glyceraldehyde-3-P by glyceraldehyde-3-phosphate dehydrogenase (GAP-DH) and the oxidation of NADH. Glyceraldehyde-3-P is converted to digydroxyacetone-P by triosephosphate isomerase (TIM), and dihydroxyacetone-P is converted to glycerol-3-P by glycerol-3-phosphate dehydrogenase (GDH) and the oxidation of NADH. The oxidation of the two NADH molecules can be monitored spectrophotometrically at a wavelength of 340 nm. Where necessary, standard curves can be prepared with standard solutions of 2,3-DPG. A kit useful in such methods is commercially available from Roche Diagnostics Corporation—Roche Applied Science (Indianapolis, Ind.), for the determination of 2,3-DPG in blood in the range of 0.02-0.15 µmol. The difference between the 2,3-DPG before and after blood has been rejuvenated can be determined.

In another method, as an alternative to measuring 2,3-DPG, the partial pressure of O2 gas required to achieve 50% hemoglobin saturation (P50) is measured. For example, the P50 can be measured at a point of care by use of a GEM Premier 3000 (Instrumentation Laboratory Company, Bedford, Mass.). In particular, a blood sample is mixed with heparin to prevent coagulation. Then, a drop or two of the blood sample is expelled onto a gauze pad. The gauze pad is then positioned at the GEM Premier 3000 for the P50 analysis. This analysis can be performed before and after the blood has been rejuvenated.

ATP can be detected in blood by a bioluminescence assay. One such assay utilizes luciferase (typically recombinant firefly luciferase), which in the presence of ATP, converts luciferin to oxyluciferin. The oxyluciferin is produced in an electronically excited state. Therefore, the oxyluciferin releases a photon of light as it returns to its ground state. To measure the ATP present in blood, a blood sample can be drawn from a patient or from tubing containing treated or untreated blood. A small sample of the blood can be mixed with a luciferin/luciferase solution. The solution can be a buffer, such as a Tricine buffer, pH 7-8, containing luciferin, luciferase, and Mg2+. The ATP in the blood sample will activate the reaction, which results in luminescence. The luminescence can be detected in a luminometer. Measurements can be taken before and after blood has been rejuvenated. Although the reagents for this ATP assay are individually available through multiple vendors, some vendors offer kits that comprise all the reagents. One such kit is the ATP Determination Kit (A22066) from Molecular Probes, Inc. (Eugene, Oreg.; now Life Technologies, Carlsbad, Calif.).

The blood may be incubated with an RBC enhancement composition for a predetermined time, such as from about 30 seconds to about 24 hours. If the blood is to be stored prior to administration, incubation may occur throughout the period in which blood is stored, as discussed further below. For example, the blood can be incubated with an RBC enhancement composition for from about 5 minutes to about 90 minutes, or from 15 minutes to about 60 minutes, at a temperature of from about 1° C. to about 45° C., or from about 25° C. to about 40° C., such as at about 37° C. In some embodiments, the blood is incubated for about 30 minutes.

Incubation can be performed using a variety of devices and methods among those known in the art. For example, blood can be incubated by immersing a bag containing the mixture of blood and RBC enhancement composition in a recirculating water bath. In another embodiment, incubating can be performed for about 5 minutes to about 60 minutes (such as for about 30 minutes) in a thawing device with a bath temperature set at from about 25° C. to about 45° C. Thawing devices include ThermoLine Models: MT202, MT204, or MT210 sold by Helmer Scientific, Noblevilles, Ind., USA, (formerly ThermoGenesis, Corp, Rancho Cordova, Calif., USA). In another example, incubating can be performed by placing the treated blood composition in an insulated box containing about 6 instant hot gel packs, wherein the temperature within the insulated box is from about 25° C. to about 45° C. A device can be placed within the insulated box to mix the treated blood composition, or the insulated box can be rotated in such a way that the treated blood composition is mixed from within.

The treated fresh blood may be stored after incubation, or may be administered to a mammalian subject in need of blood. Conditions for storage include those discussed above. In some embodiments, the administration is at a time proximate to the time when the blood is obtained and treated using methods of the present technology.

Methods may further comprise washing the blood after incubation to remove all, or a portion, of the components of the RBC enhancement composition. Washing can be performed using methods among those known in the art, including such methods as are used for processing frozen blood to remove glycerol prior to transfusion. For example, washing may comprise adding a wash solution to a liquid volume of RBCs, centrifuging the resulting mixture to form a pellet of RBCs, and removing the supernatant. Wash solutions may include, for example, normal saline. Such washing may be performed with devices known in the art, such as the ACP® 215 Automated Cell Processor, sold by Haemonetics Corporation, Braintree, Mass. The washing may be performed at a time proximate to administration of the blood to a mammalian subject.

The present technology provides methods of processing blood, which may or may not be leukocyte reduced. Such methods comprise:
 (a) obtaining whole blood from a donor;
 (b) removing leukocytes from the blood, to produce a volume of leukoreduced blood;
 (c) mixing the leukoreduced blood with an RBC enhancement composition; and
 (d) incubating the mixture of leukoreduced blood and RBC enhancement composition.

Such leukoreduced blood contains fewer leukocytes than whole blood, and may, in some embodiments, be essentially free of leukocytes. Other blood components may also be removed from leukoreduced blood, either before, during, or after removal of the leukocytes.

Methods for removing leukocytes from blood include those well known in the art. Non-limiting examples of methods for removing leukocytes from blood include centrifugation, leukocyte filtration, sedimentation, washing, freeze-thawing, and apheresis. In various embodiments, this step may be performed prior to storage of blood or upon removal of blood from storage, prior to the mixing and incubating steps. It is understood that, in some embodiments, the mixing of leukoreduced blood may be performed by a health care provider (for example, during the processing of blood prior to storage or during a medical procedure) using leukoreduced blood that has been obtained from a third party, wherein the one or both of the obtaining and removing steps of the process have been performed by the third party. Thus, methods of the present technology may comprise providing leukoreduced blood, by obtaining such blood from a third party or by performing the steps of obtaining blood and removing leukocytes from the blood, prior to the mixing step.

Without limiting the scope of methods, composition and uses of the present technology, the present technology provides methods of processing RBCs, either concurrently or post storage prior to transfusion, that will increase the metabolic activity of RBCs (for example, in the glycolysis, pentose phosphate, and amino acid pathways), restoring a metabolic profile in the RBC close to those in fresh RBC. This restored profile may result in improved RBC function in the transfusion recipient including oxygenation of tissues, nitric oxide production capacity, and reduced risk of adverse effect from the transfusion. In some embodiments, the RBC processing solution is added to fresh RBCs at a time proximate to blood collection in order to result in RBCs with a metabolic profile better than that of fresh RBCs or RBCs in a donor's circulation.

As stated above, the concentration of ATP in stored RBCs decreases during storage. In addition, the concentration of 2,3-DPG is significantly reduced after 14 days of storage and is depleted after 21 days. Methods of the present technology may restore levels of both ATP and 2,3-DPG to at least normal in stored RBCs using a RBC enhancement composition of the present technology. In some embodiments, such as where RBCs are treated proximate to the time it is withdrawn from the donor, levels of ATP and 2,3-DPG in treated RBCs may be elevated relative to levels in untreated blood.

Methods of the present technology may restore, in whole or in part, the profile of other metabolically-significant compounds in RBCs that are adversely affected by storage lesions. For example, methods of the present technology may increase nitric oxide ("NO") bioavailability. RBCs may exhibit a role in the control of tissue perfusion by release of oxygen and NO. Protein S-nitrosylation of hemoglobin (the binding of a NO-group to the thiol portion of the amino acid cysteine) is considered a major mechanism through which NO exerts its influence in vivo. Furthermore, decreases in S-nitrosylated hemoglobin occurs during storage and that re-nitrosylation of hemoglobin may correct NO bioavailability. Accordingly, the present technology provides methods of improving NO bioavailability in RBCs, by
(1) mixing blood with an RBC enhancement composition; and
(2) incubating the mixture of blood and RBC enhancement composition.

The blood may be leukoreduced, as discussed above. Additionally, methods of the present technology may improve the profile of other metabolically-significant compounds in RBCs that have not yet been affected by storage lesions.

The present technology also provides methods of administering treated blood to mammalian subjects. Methods comprising administering treated blood, in which levels of RBC components (such as ATP, 2,3-DPG and NO) are at, or elevated above, base-line levels (i.e., the level of such components in fresh blood), may be particularly advantageous in subjects having reduced tissue oxygenation as a result of impaired RBC level or function. An increase in the NO in the microcirculation may result in increased blood flow and improved oxygen delivery capability of the blood. Additionally, ATP released from red blood cells can result in the release of NO from endothelial cells, resulting in vasodilation. The present technology thus provides methods of treating a disorder characterized by reduced tissue oxygenation in a mammalian subject, comprising:
(1) mixing blood with an RBC enhancement composition;
(2) incubating the mixture of blood and RBC enhancement composition; and
(3) administering the incubated blood to the subject.

Such disorders include those wherein when blood flow is fixed, restricted, reduced, or stopped. Furthermore, blood transfusions can be necessary when blood is lost though injury, surgery or disease. Subjects and disorders that may be treated include: subjects with sepsis or septic shock that are anemic and require a blood transfusion; subjects with Upper Gastrointestinal Bleeding ("UGIB") that are anemic and require a blood transfusion; subjects subjected to severe trauma that are anemic and require a blood transfusion; subjects that are critically ill (adult and pediatric) in an intensive care unit, who are anemic and require a blood transfusion; subjects that undergo open heart surgery and receive a blood cardioplegia solution to perfuse the heart during hypothermic, ischemic cross-clamp, thus providing better oxygenation of the myocardium during open-heart surgery; subjects suffering a stroke, treating ischemic brain tissue following a stroke, thus increasing the oxygen delivery capacity of the systemic circulation via exchange transfusion or by direct administration to the ischemic area via arterial catheter or by retrograde perfusion via the venous circulation; subjects undergoing obstetrical complications, subjects with bleeding ulcers; subjects with hemolytic anemia; and subjects with thrombocytopenia.

Methods and compositions among those of the present technology are illustrated in the following non-limiting examples.

EXAMPLE 1

Whole blood (WB) samples were collected (450 or 500 mL) in CPD solution (containing sodium citrate, sodium phosphate and dextrose) from 28 normal donors. A portion of the blood (n=14) were leukoreduced ("LR"); the remaining portion (n=14) were not leukoreduced ("NLR"). All RBC were stored in AS-1 (Adsol® preservative) at 1-6° C. for 42 days prior to processing ("rejuvenation") with an RBC enhancement composition (1 hour at 37° C.). RBCs were cryopreserved (40% W/V glycerol at −80° C.), thawed after a minimum of 7 days and deglycerolized using a COBE 2991 cell processor (available from Terumo BCT, Inc.). Packed RBC content was determined by weight, and samples were collected on day 42, day 42 post rejuvenation, and post deglycerolization and tested for hemolysis, ATP, and 2,3-DPG using standard methods. The differences between LR-RBC and NLR-RBC were evaluated with unpaired t-tests at each of the 3 sample points, significance p<0.05.

LR-RBC pre-rejuvenated packed cell weights were not statistically different from NLR-RBC; 350+18 grams for LR-RBC and 338+20 grams, respectively (p<0.11). No significant difference was observed in % hemolysis between samples obtained from LR-RBC and NLR-RBC at day 42, after rejuvenation or after deglycerolization (Table 1, below).

TABLE 1

Rejuvenation of LR-RBC results in higher 2,3-DPG than with NLR-RBC. Difference between treated sample types at each sample point (n = 14)
*p < 0.05 †n = 13.

| Sample | Sample Type | ATP (μmol/g-Hb) | 2,3-DPG (μmol/g-Hb) | Hemolysis (%) |
|---|---|---|---|---|
| Day 42 | LR-RBC | 3.2 ± 0.6* | 0.2 ± 0.1* | 0.5 ± 0.4 |
|  | NLR-RBC | 2.6 ± 0.6* | 0.1 ± 0.1* | 0.9 ± 0.5 |
| Post Rejuvenation | LR-RBC | 7.9 ± 1.1† | 11.0 ± 1.5*† | 0.5 ± 0.4 |
|  | NLR-RBC | 7.6 ± 0.7 | 8.1 ± 1.6* | 0.7 ± 0.3 |
| Deglycerolized | LR-RBC | 7.5 ± 0.5 | 16.7 ± 1.6* | 0.4 ± 0.1 |
|  | NLR-RBC | 7.8 ± 0.7 | 13.9 ± 1.9* | 0.3 ± 0.1 |

Both ATP and 2,3-DPG increased following rejuvenation of LR-RBC and NLR-RBC. No difference in ATP was observed between LR-RBC and NLR-RBC; however, 2,3-DPG concentration was higher in LR-RBC when compared to NLR-RBC after rejuvenation. The results demonstrate that pre-storage leukocyte reduction of RBC may alter or attenuate RBC lesions during storage, as higher ATP and 2,3-DPG levels pre-rejuvenation were observed and higher 2,3-DPG synthesis occurred following processing with the RBC processing solution in leukoreduced RBCs when compared to RBCs that were not leukocyte reduced prior to storage.

EXAMPLE 2

RBC (CPD/AS-1) were prepared from 4 subjects, stored at 1-6° C. for 42 days, followed by processing ("rejuvenation") with an RBC enhancement composition of a 5 mL aliquot (1 hour at 37° C.). Samples were collected on day 42 and day 42 post rejuvenation (no wash) and tested for hemolysis, ATP, and 2,3-DPG. Additional samples were immediately frozen at −80° C. for metabolomic analysis using GC/MS and LC/MS/MS platforms and a proprietary library for metabolite identifications. Data were normalized to protein content, transformed and standardized within the experiment. Matched-pair t-tests were used to identify significant differences in biochemicals (p<0.05) pre and post rejuvenation.

The maximum hemolysis observed at day 42 (before and after rejuvenation) was 0.6%. ATP (μmol/g-Hb) fell from 3.5±0.5 (day 0) to 2.6±0.3 (day 42) and was restored to 7.0±1.6 by rejuvenation. 2,3-DPG (μmol/g-Hb) was depleted at day 42 (16.0±2.8 day 0 to 0.3±0.2) and restored to 8.3±2.3. There were significant changes in relative concentrations in 88 of 270 identified biochemicals (33%) following rejuvenation. This included 61% of the metabolites in carbohydrate pathways revealing increased activity in glycolysis and the pentose phosphate pathway. Pathways associated with amino acid and lipid metabolism were also affected (Table 2, below).

TABLE 2

Changes in Relative Concentrations of Biochemicals Day 42 Post RBC Rejuvenation (p ≤ 0.05).

| Pathway Category | Number (%) of changed biochemicals (increased↑, decreased↓ post rejuvenation) | Total Biochemicals |
|---|---|---|
| Total | 88 (33%) 64↑, 24↓, | 270 |
| Carbohydrate | 22 (61%) 21↑, 1↓ | 36 |
| Amino Acid | 20 (26%) 3↑, 17↓ | 76 |
| Lipid | 30 (29%) 27↑, 3↓ | 103 |
| All Other Pathways | 16 (29%) 13↑, 3↓ | 55 |

This study indicates that use of the RBC enhancement composition is able to significantly alter the concentrations of 33% of the identified RBC biochemicals.

The embodiments and the examples described herein are exemplary and not intended to be limiting in describing the full scope of compositions and methods of the present technology. Equivalent changes, modifications and variations of embodiments, materials, compositions and methods can be made within the scope of the present technology, with substantially similar results.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition or method.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested. Equivalent changes, modifications and variations of some embodiments, materials, compositions and methods can be made within the scope of the present technology, with substantially similar results.

As used herein, the words "preferred" or "preferable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

What is claimed is:

1. A method for restoring a metabolic profile in red blood cells (RBCs), comprising:
   a) obtaining whole blood from a donor;
   b) removing leukocytes from the whole blood, to produce a volume of leukoreduced blood;
   c) mixing the leukoreduced blood with an RBC enhancement composition comprising a rejuvenating material selected from the group consisting of inosine, adenine, pyruvate, phosphate, and mixtures thereof; and
   d) incubating the mixture of leukoreduced blood and RBC enhancement composition, thereby restoring the metabolic profile in the RBCs and forming treated leukoreduced RBCs; and
   e) administering the treated leukoreduced RBCs to a subject in need thereof,
   wherein the levels of one or both of adenosine triphosphate (ATP) and 2,3-diphosphoglycerate (2,3-DPG) in the treated leukoreduced blood after the step of incubating are restored to levels equal to or greater than the levels of ATP and 2,3-DPG found in fresh blood, and wherein the removing, mixing, incubating, and administering are performed within 24 hours of the obtaining of the whole blood from the donor.

2. The method for restoring a metabolic profile in RBCs according to claim 1, wherein levels of both ATP and 2,3-DPG in the leukoreduced blood after the step of incubating are at least restored to levels of ATP and 2,3-DPG in fresh blood.

3. The method for restoring a metabolic profile in RBCs according to claim 1, wherein the RBC enhancement composition comprises from about 25 g/L to about 30 g/L inosine, from about 0.2 g/L to about 2 g/L adenine, from about 5 g/L to about 15 g/L pyruvate, and from about 17 g/L to about 23 g/L sodium phosphate.

4. The method for restoring a metabolic profile in RBCs according to claim 1, wherein the incubating is at a temperature of from about 1° C. to about 45° C., for a pre-determined period of time.

5. A method for treating a disorder characterized by reduced tissue oxygenation in a mammalian subject, comprising:
   a) obtaining whole blood from a donor;
   b) removing leukocytes from the whole blood, to produce a volume of leukoreduced blood;
   c) mixing the leukoreduced blood with an RBC enhancement composition comprising inosine, adenine, pyruvate, and phosphate;
   d) incubating the mixture of leukoreduced blood and RBC enhancement composition, thereby restoring the metabolic profile in the RBCs and forming treated leukoreduced RBCs; and
   e) administering the incubated blood to the subject
   wherein the levels of one or both of adenosine triphosphate (ATP) and 2,3-diphosphoglycerate (2,3-DPG) in the treated leukoreduced blood after the step of incubating are restored to levels equal to or greater than the levels of ATP and 2,3-DPG found in fresh blood, and wherein the removing, mixing, incubating, and administering are performed within 24 hours of the obtaining of the whole blood from the donor.

6. The method according to claim 5, wherein the blood is autologous to the subject.

7. The method for treating a disorder according to claim 5, wherein the RBC enhancement composition comprises from about 25 g/L to about 30 g/L inosine, from about 0.2 g/L to about 2 g/L adenine, from about 5 g/L to about 15 g/L pyruvate, and from about 17 g/L to about 23 g/L sodium phosphate, and has a pH from about 6.7 to about 7.1.

8. The method for treating a disorder according to claim 5, further comprising washing the blood immediately prior to administering the blood to the subject.

9. The method for treating a disorder according to claim 5, wherein the disorder is sepsis, septic shock, Upper Gastrointestinal Bleeding (UGIB), anemia, severe trauma, heart attack or stroke.

10. The method for treating a disorder according to claim 5, wherein the subject is undergoing surgery and is in need of a blood transfusion.

11. The method for treating a disorder according to claim 10, wherein the surgery is open heart surgery.

* * * * *

UNITED STATES PATENT AND TRADEMARK OFFICE
CERTIFICATE OF CORRECTION

| | | |
|---|---|---|
| PATENT NO. | : 9,066,909 B2 | Page 1 of 1 |
| APPLICATION NO. | : 13/756021 | |
| DATED | : June 30, 2015 | |
| INVENTOR(S) | : Alan Gray | |

It is certified that error appears in the above-identified patent and that said Letters Patent is hereby corrected as shown below:

In the claims

In column 12, line 9, in Claim 2, after "the", insert --treated--, therefor

Signed and Sealed this
Fifteenth Day of December, 2015

Michelle K. Lee
*Director of the United States Patent and Trademark Office*